United States Patent [19]

Möstl et al.

[11] Patent Number: 5,243,982
[45] Date of Patent: Sep. 14, 1993

[54] DEVICE FOR DETERMINING THE CONCENTRATION OF AT LEAST ONE SUBSTANCE IN ORGANIC TISSUE

[75] Inventors: Anton Möstl; Michael Mayer, both of Graz, Austria

[73] Assignee: AVL Medical Instruments AG, Schaffhausen, Switzerland

[21] Appl. No.: 732,401

[22] Filed: Jul. 18, 1991

[30] Foreign Application Priority Data

Jul. 19, 1990 [AT] Austria ................. 1530/90

[51] Int. Cl.$^5$ .............................. A61B 5/00
[52] U.S. Cl. .................... 128/632; 128/DIG. 12; 604/153
[58] Field of Search ............ 604/27, 30, 35, 153–155, 604/191, 65–67, 891.1; 128/632, 633, 635, DIG. 12

[56] References Cited

U.S. PATENT DOCUMENTS

| | | | |
|---|---|---|---|
| 3,405,706 | 10/1968 | Cinqualbre | 604/191 |
| 4,676,256 | 6/1987 | Golden | 604/191 |
| 4,689,042 | 8/1987 | Sarnoff et al. | 604/191 |
| 4,784,157 | 11/1988 | Halls et al. | 604/191 |
| 4,795,441 | 1/1989 | Bhatt | 604/191 |
| 4,846,797 | 7/1989 | Howson et al. | 128/DIG. 12 |
| 4,850,972 | 7/1989 | Schulman et al. | 604/67 |
| 4,957,490 | 9/1990 | Byrne et al. | 604/110 |
| 5,097,834 | 3/1992 | Skrabal | 128/DIG. 13 |

FOREIGN PATENT DOCUMENTS 0367752 10/1989 European Pat. Off. .

OTHER PUBLICATIONS

International Publication No. WO88/05643, published 11 Aug. 1988, to Falko Skrabal.

Primary Examiner—Lee S. Cohen
Assistant Examiner—Samuel Gilbert
Attorney, Agent, or Firm—Watson, Cole, Grindle & Watson

[57] ABSTRACT

A device for determining the concentration of at least one substance in organic tissue includes a subcutaneous needle for insertion into the tissue and a pumping and suction unit which is controlled by a microprocessor and is used for delivering a perfusion fluid and draining it after its partial equilibration with the tissue. The device further includes a sensing unit connected to the microprocessor for determining the concentration of the substance to be analyzed and one or more marker variables. The perfusion fluid, a calibrating solution and at least one drug are provided in replaceable metering ampoules sealed with membranes, whose metering plungers can be actuated by a drive unit controlled by the microprocessor. The metering ampoules communicate with a master capillary leading from the pumping and suction unit to the subcutaneous needle; communication is established via capillary tubes piercing the membranes.

13 Claims, 2 Drawing Sheets

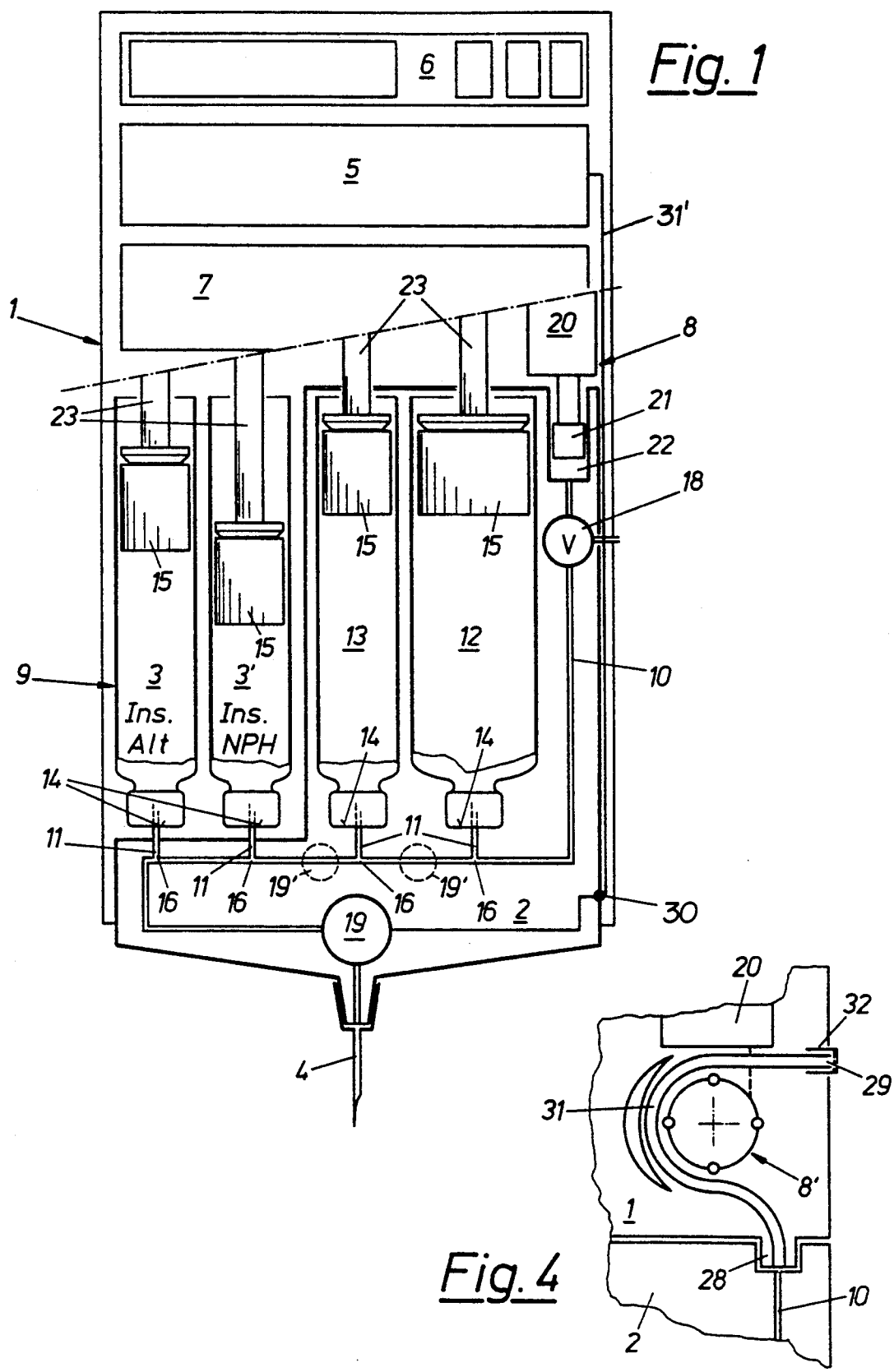

DEVICE FOR DETERMINING THE CONCENTRATION OF AT LEAST ONE SUBSTANCE IN ORGANIC TISSUE

BACKGROUND OF THE INVENTION

This invention relates to a device for determining the concentration of at least one substance in organic tissue, including a hypodermic needle for insertion into the tissue, a pumping and suction unit provided in a housing, which unit is controlled by a microprocessor and is used for delivering a perfusion fluid and draining it after its partial equilibration with the tissue, and further including a sensing unit connected to the microprocessor for determining the concentration of the substance to be analyzed and one or more marker variables, as well as containers for the perfusion fluid, for a calibrating solution and at least one drug.

DESCRIPTION OF THE PRIOR ART

In medical applications it is often necessary to analyze the composition of body fluids repeatedly or continuously so as to be able to detect and remove disturbances of the homeostasis. The need for frequent blood sampling has been eliminated by the development of devices delivering a steady flow of information on the patient.

In WO 88/05643, for instance, a pen-shaped device referred to as "glucose-pen" is described, which has a hypodermic needle at its end for insertion into the tissue. The pen-shaped housing contains a plunger pump with a reservoir for the perfusion fluid, whose plunger may be used both for pumping the perfusion fluid out of the reservoir and delivering it into the collecting vessel opening up behind the plunger. The perfusion fluid is delivered to openings in the wall of the hypodermic needle through a first channel in this needle, thus coming into contact with the tissue, and is taken to the collecting vessel through a second channel, which may be concentric with the first, by means of the prevailing suction. As close to the hypodermic needle as possible an anlyzing unit is installed adjacent to the drainage tube for the perfusion fluid, carrying a measuring capillary for the substance to be analyzed and for a marker variable. Relevant marker variables are the conductivity or ionic concentration of the perfusion fluid, for example, the measured values permitting the degree of interaction between perfusion fluid and tissue to be calculated and the actual concentration of the substance of interest (e.g., glucose) to be subsequently determined, even in the instance of only partial equilibration of the perfusion fluid with the tissue.

The use of a device of the above kind as published in EP-A 0 367 752, an enhanced variant of the subject of WO 88/05643, will eliminate the need for multi-channel hypodermic needles, whose manufacture is complicated. This device is based on the use of a single-channel needle whose channel is directly connected with the analyzing unit or the sensing unit. The analyzing unit is connected with a plunger pump which may be used for reversing the direction of flow of the perfusion fluid in the channel of the hypodermic needle. By means of this very simple device a few microliters of the perfusate are pumped into the hypodermic needle after it has been inserted into the patient's body, the perfusion solution passing through the analyzing unit and enabling zero-point calibration. After partial equilibration of the perfusate with the tissue surrounding the hypodermic needle, the fluid is sucked out of the needle and again brought into contact with the sensors of the analyzing unit, the substance to be determined and the marker variable being measured and the actual concentration being calculated from the values obtained.

The only disadvantage of this perfectly functional device is that it may be awkward to handle or refill with the various fluids, such as calibrating solution, perfusion fluid, or the particular drug used.

SUMMARY OF THE INVENTION

It is an object of the invention to develop and improve a device of the above type in such a way as to make it easy to handle even for medical or technical laymen, and to permit simple maintenance jobs, such as the refilling and replacing of spent materials to be carried out quickly.

In the invention this is achieved by providing the perfusion fluid, the calibrating solution and the drug in replaceable metering ampoules sealed by membranes, whose metering plungers are actuated by a drive unit controlled by the microprocessor, and by providing that the metering ampoules communicate with a master capillary leading from the pumping and suction unit to the hypodermic needle, communication being established via capillary tubes piercing the membranes. In this manner handling is simplified and the device is made less expensive, since conventional drug ampoules available on the market, such as insulin ampoules, may be directly used. The perfusion fluid and the calibrating solution may be filled into standard-size ampoules, eliminating the necessity of specially manufactured containers.

Although the devices disclosed in EP-A 0 293 958 and EP-A 0 362 484 are provided with insulin ampoules whose membranes are pierced by a needle unit upon use, these devices do not permit the delivery of a perfusion fluid into the patient's body, nor the collecting or measuring of this fluid.

In the invention the device is further simplified by providing the entrance points of the capillary tubes into the master capillary with check valves which will open at a defined level of excess pressure in the capillary tubes. In this way the multiway valve required for the device in EP-A 0 367 752, for example, is made superfluous, together with its drive element.

The check valve may comprise a piece of flexible tubing inserted into the master capillary, which is placed at the entrance point of the capillary tube, sealing the latter or opening it at an excess pressure level inside the capillary tube. Other types of non-energized, pressure-controlled valves could be used, of course, such as a spring-loaded ball pressed against a valve seat and opening upon the application of excess pressure.

It will be a special advantage if the device of the invention is configured as a four-part assembly comprising (1) a housing containing the microprocessor and a communication unit attached thereto, the drive unit for the metering ampoules and the pumping and suction unit, a receiving position for one or more drug metering ampoules as well as the energy supply;

(2) a replaceable unit to be inserted into the housing, which unit holds the sensing unit, the master capillary together with its capillary branches and the metering ampoules for the perfusion fluid and the calibrating solution;

(3) one or more drug metering ampoules to be inserted into the receiving position of the housing, which may be connected to the specific capillary tubes in the replaceable unit provided for this purpose;

(4) a hypodermic needle to be attached to the replaceable unit.

To ensure simplicity of handling, the device of the invention thus consists of very few separate components, such as a housing, drug ampoules, a replaceable unit (to be called KIT in the following) and a needle. Apart from the housing, which contains the microprocessor, the communication unit, the drive mechanism and the pumping and suction unit of the device, all other components are consumable parts which may be easily replaced by the user. All the patient has to do is replace empty drug ampoules, or the KIT (in the instance of empty metering ampoules or faulty sensors) or a needle that is blunt or no longer sterile.

It is further provided by the invention that the pumping and suction unit be configured as a plunger pump which is located in the housing of the device together with its drive mechanism, the plunger chamber of the pump being connected with the master capillary in the replaceable unit by means of a coupling.

Like the device disclosed in EP-A 0 367 752, the device of this invention also benefits from separating the individual fluids of the system by means of an air bubble, for which purpose a valve for ventilation of the master capillary may be provided next to the pumping and suction unit, which valve is controlled by the microprocessor.

A particularly simple variant of the invention provides that the ventilation valve be furnished with a movable element which can be shifted between two extreme positions, preferably by means of an electromagnet, the pumping and suction unit being connected to the hypodermic needle in one extreme position, and to the ambient air in the other extreme position of this movable element.

For further reduction of mechanical and electrical connections between the housing and the replaceable unit, the proposal is put forward that the movable element of the ventilation valve and at least one electromagnet actuating this element be placed in the housing of the device.

It is provided in a particularly favorable variant of the invention that the pumping and suction unit be configured as a peristaltic pump to be put into the housing of the device together with its drive mechanism, one end of the tube of this pump being connected to the master capillary in the replaceable unit by means of a coupling, and the other end being connected to an opening into the ambient air, which is covered by a filter.

To enhance the modular design of the device, it is proposed that the drive unit include a microprocessor-controlled motor with gear for each metering ampoule as well as a driving rod actuating the metering plunger in the ampoule.

The device of the invention is particularly well suited for determining the concentration of glucose and for the automatic administration of insulin, if the sensing unit is provided with sensors for measuring glucose concentration and the conductivity of the perfusion fluid, and if metering ampoules are provided for regular insulin and/or NPH insulin.

BRIEF DESCRIPTION OF THE DRAWINGS

The invention will now be further described by way of example only with reference to the accompanying drawings, in which FIG. 1 shows a partial section of a device of the invention, FIG. 4 shows a detail of a variant of the invention of FIG. 1.

DETAILED DESCRIPTION OF PREFERRED EMBODIMENTS

Figure 2A:
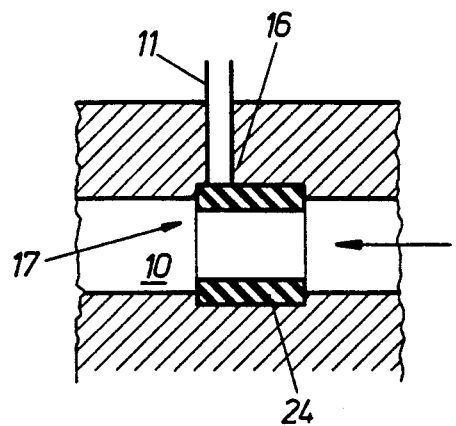
FIGS. 2a, 2b and 3a, 3b show a detail of the invention in two operating states each.

The device presented in FIG. 1 is a glucose-insulin-pen; however, other uses are possible.

The device comprises a housing 1, a replaceable unit or KIT 2 to be inserted into the housing 1, drug ampoules 3, 3', and a hypodermic needle 4 to be attached to the replaceable unit.

The housing 1 contains a microprocessor 5, which is connected to a communication unit 6, via which the device is controlled by the patient using pushbuttons and an optical/acoustic display. The housing 1 further contains a drive unit 7 for the metering ampoules 3, 3' for the drug, and for the metering ampoules in the KIT to be described below, and for the pumping and suction unit configured as a plunger pump 8 in FIG. 1. In addition, the housing 1 has a receiving position 9 for the drug ampoules 3, 3' and the energy supply (such as simple or rechargeable batteries), not shown here.

The KIT 2 for insertion into the housing 1 is a compact plastic component with a master capillary 10 leading from the attachable hypodermic needle 4 to the pumping and suction device 8, which master capillary 10 receives the individual capillary tubes 11. The KIT 2 is provided with a metering ampoule 12 for the perfusion fluid simultaneously used as zero-point-solution (N solution) and a metering ampoule 13 for the calibrating solution (S solution).

The individual metering ampoules 3, 3', 12, 13 are sealed by membranes 14, which are punctured by the capillary tubes 11 upon insertion into the receiving position 9, or rather, the KIT 2, such that a connection to the master capillary 10 is established. The ampoules have metering plungers 15 which are actuated by the drive unit 7 controlled by the microprocessor 5.

Figure 2B:
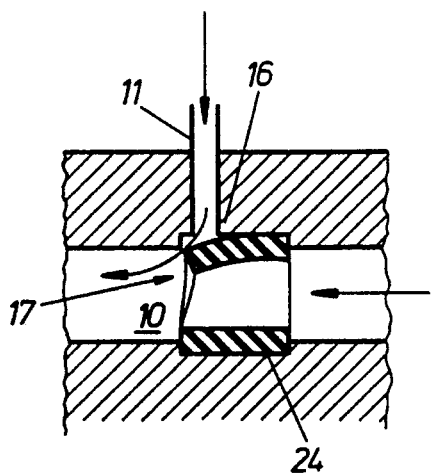

At the points of entrance 16 of the capillary tubes 11 into the master capillary 10 are located the check valves 17 presented in detail in FIGS. 2a and 2b, which will open at a given level of excess pressure. Next to the plunger pump 8 the master capillary 10 is provided with a ventilation valve 18 controlled by the microprocessor. At the needle end of the KIT the master capillary 10 goes through the sensing unit 19 with its sensors for determining glucose concentration and conductivity. It would also be possible to put the sensing unit in some other place along the master capillary 10, e.g., in positions 19' indicated by a broken line. The electric connection between the sensor 19 and the housing 1 is established via a contact 30 when the KIT 2 is inserted into the housing 1. The contact 30 is electrically connected to the microprocessor 5 by a wire 31'.

As is shown in FIG. 1, the pumping and suction unit may be configured as a plunger pump 8, whose drive unit 20 is located in the housing 1 together with its plunger 21, and whose plunger chamber 22 communicating with the master capillary 10 is located in the replaceable unit 2.

For each metering ampoule 3, 3', 12, 13 the drive unit is provided with a motor with gear 7' and a driving rod 23 acting on the metering plunger 15, which may be part of the housing 1 or the respective metering ampoule.

FIGS. 2a and 2b show a variant of a check valve 17 provided with a piece of flexible tube 24 to be inserted into the master capillary 10, which tube is located at the entrance point 16 of the capillary tube 11. In the instance of excess pressure (FIG. 2b) the piece of tube is deformed and the capillary tube 11 is opened. Basically, any type of check valve would be suitable such as a ball and spring unit, for example.

It is an advantage as shown in a variant in two operating states 3a and 3b if both the ventilation valve 18 and the plunger pump 8 are located in the housing 1 of the device. The plunger chamber 22 of the plunger pump 8 is connected to the master capillary 10 in the replaceable unit 2 via a coupling 28. When the unit 2 is inserted into the housing 1 a gas- and liquid-tight connection is established.

Figure 3A:
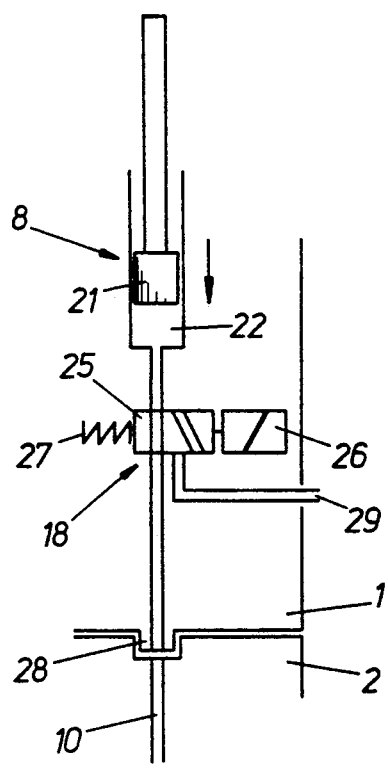
Figure 3B:
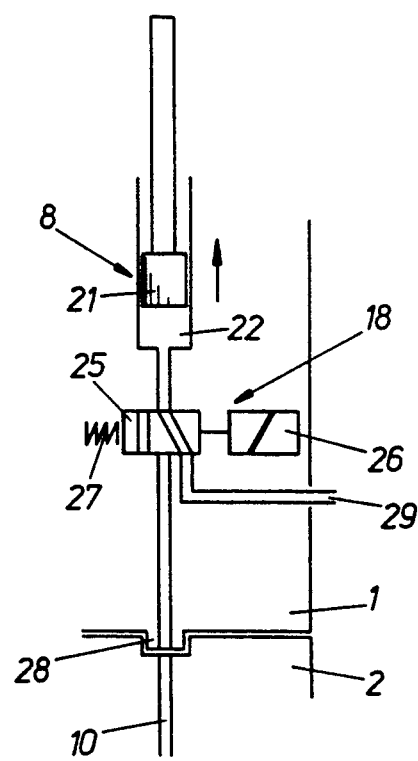

The ventilation valve 18 has a slide element 25 which may be shifted between two extreme positions and which is moved by an electromagnet 26 in the housing 1 against the force of a spring 27, connecting the plunger pump 8 with the master capillary 10 leading to the hypodermic needle in one extreme position (FIG. 3a), and with the ambient air via the opening 29 in the other extreme position. Again, other known types of two-way valves may be used.

In a variant shown in FIG. 4 a peristaltic pump 8' is provided as a pumping and suction unit, which is placed in the housing 1 of the device together with its drive unit 20. One end of the tube 31 of the pump 8' is connected to the master capillary 10 in the replaceable unit 2 by means of the coupling 28; the other end leads to an opening 9 covered by a bacteriological filter 32, through which ambient air may be drawn. This variant does not require a controlled valve.

The device illustrated by FIG. 1 provides receiving positions for two insulin ampoules. Depending on the kind of therapy needed for diabetic patients of type I or type II the appropriate insulin ampoules may be inserted into these positions.

The usage period of the insulin ampoules is determined by the number of applications and the insulin doses. Normally, the insulin ampoules will be used up before the KIT 2 needs replacing. In the device of the invention the insulin ampoules are exchanged independently of any replacement of the KIT. If an ampoule is ready for replacement this is indicated by the communication unit 6 of the device, and the corresponding ampoules are automatically released for removal.

The patient is only required to remove the empty ampoules from the device and discard them, and to insert new ampoules and make the device ready for operation by pushing a button.

Besides, the patient must replace the old KIT by a new one from time to time, depending on the amount of calibrating solution or perfusion fluid used for each measurement and the dimensioning of the corresponding metering ampoules.

The device will indicate if the KIT needs replacing, releasing the empty KIT for removal at the same time. After the KIT has been replaced the device is switched back to operating mode by the pushing of a button.

The KIT and the hypodermic needle are delivered to the patient in sterile packaging. Insulin ampoules are delivered in standard packaging.

We claim:

1. A device for determining a concentration of at least one substance in organic tissue, comprising
    a subcutaneous needle which is insertable into said organic tissue,
    a microprocessor and a sensing unit means which is connected to said microprocessor for determining the concentration of said substance to be determined and at least one endogenous or exogenous marker variable of a perfusion fluid,
    a pumping and suction unit means for feeding said perfusion fluid into said subcutaneous needle and for draining said perfusion fluid after partial equilibration with said at least one substance, said pumping and suction unit means being controlled by said microprocessor,
    replaceable metering ampoules sealed with membranes containing said perfusion fluid, a calibrating solution and at least one drug, and drive unit means for actuating metering plungers of said metering ampoules, said drive unit means controlled by said microprocessor, and wherein said metering ampoules communicate with a master capillary leading from said pumping and suction unit means to said subcutaneous needle, communication being established via capillary tubes piercing said membranes of said metering ampoules.

2. A device according to claim 1, wherein all entrance points of said capillary tubes into said master capillary are provided with check valves opening at a defined level of excess pressure inside said capillary tubes.

3. A device according to claim 2, wherein each of said check valves comprises a piece of flexible tubing inserted into said master capillary, each said piece being placed at said entrance point of said capillary tube.

4. A device according to claim 1, essentially configured as a four-part assembly comprising
    a housing, as a first part, containing said microprocessor and a communication unit attached thereto, said drive unit means for actuating said metering plungers of said metering ampoules, said pumping and suction unit, means receiving positions for at least one drug metering ampoule, a replacement unit, and an energy supply,
    a second part embracing said replacement unit insertable into said housing, said replacement unit holding said sensing unit means, said master capillary together with said capillary tubes and said metering ampoules containing said perfusion fluid and said calibrating solution,
    a third part consisting of said at least one drug metering ampoule respectively insertable into one of said receiving positions of said housing, which is connectable to one of said capillary tubes in said replacement unit, and
    a fourth part comprising said subcutaneous needle attachable to said replacement unit, said subcutaneous needle being connected with said master capillary.

5. A device according to claim 4, wherein said pumping and suction unit means is configured as a plunger pump located in said housing together with a drive mechanism of said plunger pump, a plunger chamber of said plunger pump being connected with said master capillary in said replacement unit by means of a coupling.

6. A device according to claim 5, wherein a valve means for ventilation of said master capillary is provided next to said pumping and suction unit means, said valve means being controlled by said microprocessor.

7. A device according to claim 6 wherein said ventilation valve means comprises a movable element which can be shifted between two extreme positions by means of an electromagnet, thus connecting said pumping and suction unit means to said subcutaneous needle through said master capillary in one extreme position, and to the ambient air in the other extreme position of said movable element.

8. A device according to claim 7, wherein said movable element of said ventilation valve means and at least one electromagnet actuating said movable element are placed in said housing.

9. A device according to claim 4, wherein said pumping and suction unit means is configured as a peristaltic pump located in said housing together with a drive mechanism of said peristaltic pump, one end of a tube or said peristaltic pump being connected to said master capillary in said replacement unit by means of a coupling, and the other end of said tube being connected to an opening to the ambient air, said opening being covered by a filter.

10. A device according to claim 4, wherein said drive unit means comprises a microprocessor-controlled motor with gear for each of said metering ampoules and driving rods actuating said metering plungers in said ampoules.

11. A device according to claim 4, for determining the concentration of glucose and for the automatic administration of insulin, wherein said sensing unit means is provided with sensor means of measuring glucose concentration and the conductivity of the perfusion fluid, and wherein metering ampoules are provided for regular insulin or NPH insulin.

12. A device according to claim 1, for determining the concentration of glucose and for the automatic administration of insulin, wherein said sensing unit means is provided with sensor means for measuring glucose concentration and the conductivity of the perfusion fluid, and wherein metering ampoules are provided for regular insulin or NPH insulin.

13. A device according to claim 1, wherein said drive unit means comprises a microprocessor-controlled motor with gear for each of said metering ampoules and driving rods actuating said metering plungers in said ampoules.

* * * * *

UNITED STATES PATENT AND TRADEMARK OFFICE
CERTIFICATE OF CORRECTION

PATENT NO. : 5,243,982
DATED : September 14, 1993
INVENTOR(S) : Möstl et al.

It is certified that error appears in the above-indentified patent and that said Letters Patent is hereby corrected as shown below:

On the title page, item [75] should read as follows:

Anton Möstl; Michael Mayer; Falko

Skrabal, all of Graz, Austria

Signed and Sealed this

Twenty-ninth Day of March, 1994

*Attest:*

BRUCE LEHMAN

*Attesting Officer*      *Commissioner of Patents and Trademarks*